(12) United States Patent
Merritt (10) Patent No.: US 11,510,638 B2
(45) Date of Patent: Nov. 29, 2022

(54) CONE-BEAM COMPUTER TOMOGRAPHY SYSTEM FOR PROVIDING PROBE TRACE FIDUCIAL-FREE ORAL CAVITY TRACKING

(71) Applicant: X-Nav Technologies, LLC, Lansdale, PA (US)

(72) Inventor: Scott A. Merritt, Golden, CO (US)

(73) Assignee: X-Nav Technologies, LLC, Lansdale, PA (US)

( * ) Notice: Subject to any disclaimer, the term of this patent is extended or adjusted under 35 U.S.C. 154(b) by 834 days.

(21) Appl. No.: 15/480,967

(22) Filed: Apr. 6, 2017

(65) Prior Publication Data

US 2017/0290554 A1 Oct. 12, 2017

Related U.S. Application Data

(60) Provisional application No. 62/318,963, filed on Apr. 6, 2016.

(51) Int. Cl.
*A61B 6/00* (2006.01)
*A61B 6/03* (2006.01)
(Continued)

(52) U.S. Cl.
CPC ............... *A61B 6/14* (2013.01); *A61B 6/032* (2013.01); *A61B 6/466* (2013.01); *A61B 6/488* (2013.01);
(Continued)

(58) Field of Classification Search
CPC .......... A61B 6/14; A61B 6/466; A61B 6/032; A61B 6/4085; A61C 1/082; G06T 2207/30036
See application file for complete search history.

(56) References Cited

U.S. PATENT DOCUMENTS 5,588,430 A 12/1996 Bova et al.
5,792,147 A 8/1998 Evans et al.
(Continued)

FOREIGN PATENT DOCUMENTS

EP 1871267 B1 9/2018
KR 100998311 B1 12/2010
(Continued)

OTHER PUBLICATIONS

Granger et al., Rigid Point-Surface Registration using Oriented Points and an EM Variant of ICP for Computer Guided Oral Impantology, (RR-4169, INRIA.2001 HAL Id: inria-000072453, https://hal.inria.fr/inria-00072453), 24 pages, 2001.
(Continued)

*Primary Examiner* — Serkan Akar
*Assistant Examiner* — Amal Aly Farag
(74) *Attorney, Agent, or Firm* — Faegre Drinker Biddle & Reath LLP (57) ABSTRACT

A method for referencing a tracking system's coordinate frame to a rigid body's coordinate frame is disclosed. The method involves obtaining a 3D model depicting some of the surfaces of the rigid body. A probe is provided with an affixed tracking reference component. A second tracking reference component is attached to the rigid body. The method involves tracking locations of the probe as it moves along surfaces of the rigid body and then determining a transform that relates the probe locations to the 3D model of the rigid body. In one embodiment the rigid body is a dental mandible or maxilla of a patient and the 3D model is a surface extracted from a computed tomography image of the patient's jaw and teeth.

16 Claims, 8 Drawing Sheets

(51) Int. Cl.
  *A61B 6/12*     (2006.01)
  *A61B 6/14*     (2006.01)
  *A61B 90/00*    (2016.01)
  *A61C 1/08*     (2006.01)
  *A61C 13/00*    (2006.01)
  *G06T 3/00*     (2006.01)

(52) U.S. Cl.
  CPC .............. *A61B 90/37* (2016.02); *A61C 1/082* (2013.01); *A61C 13/00* (2013.01); *A61B 6/4085* (2013.01); *A61B 90/39* (2016.02); *A61B 2090/3983* (2016.02); *G06T 3/0087* (2013.01)

(56) References Cited

U.S. PATENT DOCUMENTS

| | | | |
|---|---|---|---|
| 6,223,067 B1 | 4/2001 | Vilsmeier et al. | |
| 6,978,167 B2 | 12/2005 | Dekel et al. | |
| 7,457,443 B2 | 11/2008 | Persky | |
| 2006/0025677 A1* | 2/2006 | Verard | A61B 90/36 600/423 |
| 2006/0083422 A1 | 4/2006 | Ernst et al. | |
| 2011/0079083 A1 | 4/2011 | Yoo et al. | |
| 2011/0142354 A1* | 6/2011 | Sung | G06T 7/73 382/209 |
| 2012/0244488 A1 | 9/2012 | Chishti et al. | |
| 2014/0272773 A1* | 9/2014 | Merritt | A61B 5/0088 433/29 |
| 2015/0182296 A1* | 7/2015 | Daon | A61B 6/12 600/424 |
| 2016/0000518 A1 | 1/2016 | Thoranaghatte | |
| 2016/0074127 A1 | 3/2016 | Merritt et al. | |
| 2016/0074129 A1 | 3/2016 | Merritt et al. | |
| 2019/0046276 A1* | 2/2019 | Inglese | A61C 9/0046 |

FOREIGN PATENT DOCUMENTS

| | | |
|---|---|---|
| WO | 2006065955 A2 | 6/2006 |
| WO | 2011/162753 A1 | 12/2011 |
| WO | 2012109760 A1 | 8/2012 |

OTHER PUBLICATIONS

International Search Report and Written Opinion (ISA/US) dated Jul. 3, 2017 in corresponding International Application No. PCT/US17/26416.

Extended Search Report dated Nov. 6, 2019 in corresponding European Application No. 17779852.7.

* cited by examiner

CONE-BEAM COMPUTER TOMOGRAPHY SYSTEM FOR PROVIDING PROBE TRACE FIDUCIAL-FREE ORAL CAVITY TRACKING

RELATED APPLICATION

This application is related to and claims priority from U.S. Provisional Application 62/318963, filed on Apr. 6, 2016, the disclosure of which is incorporated herein by reference in its entirety.

FIELD OF THE INVENTION

The present invention relates to navigation systems and, more particularly, to a system and method to using a probe trace to provide fiducial free tracking on a rigid body.

BACKGROUND

Image-guided surgical placement of dental implants significantly improves accuracy of placement of the dental implants, which improves the accuracy of the dental restoration, leading to better aesthetics and improved patient comfort. Current state-of-the-art image-guided surgical implant systems use stereo cameras to track and locate tracking reference components. One tracking reference component is rigidly attached to the dental drill that will be used to deliver the implant, which allows its position and orientation to be tracked. A second tracking reference component is affixed to the teeth, gums, or bone on the jaw that will receive the implant, allowing the drill's motion to be determined relative to a fixed reference frame on the surgical jaw.

In order to be useful for image guidance, the surgical jaw's reference frame must be related back to the computed tomography (CT) volume in which the dental anatomy can be visualized, and in which the desired implant locations are defined by the surgeon. State-of-the-art systems facilitate the determination of this relation by relying upon attaching a fixture to the patient's surgical jaw, teeth, and/or gums prior to obtaining a cone-beam computed tomography (CBCT) volume. The fixture contains fiducials that are in an a prior known arrangement. The fiducials are made of material that can be located in the CBCT volume. The prior system uses the fiducials to determine the location and orientation of the fixture within the pre-operative CBCT scan. During the operation, the same fixture is replaced on the dental anatomy in the same location and the tracking reference components are attached to the fixture during surgery in order to relate pre-operative planning information to the real-time surgical tracking environment.

The conventional method for determining the relation between the real-time surgical tracking environment and the pre-operative CBCT planning environment imposes a number of limitations. Firstly, any discrepancy between where the fixture was during the CBCT scan, and where it is placed when attached during surgery results in inaccuracy of the guidance. Secondly, due to limited space within the oral cavity, the size of the fixture must be relatively small. As such, any inaccuracy grows with distance from the surgical site, this can limit accuracy. Thirdly, the requirement that the fixture be placed prior to CBCT acquisition imposes workflow burden. Surgeons often don't know whether a case is suitable for guidance until after analysis of the CBCT acquisition. The CBCT may be sent in from a referring doctor, which imposes coordination issues, and the doctors must manage an inventory of patient-specific fixtures between CBCT acquisition and time of surgery. The surgical environment also imposes additional placement constraints that may not be apparent at CBCT acquisition time, which may cause usability issues.

SUMMARY OF THE INVENTION

The present invention overcomes the limitations of the prior art by determining the relationship between the pre-operative CBCT and the real-time surgical environment without the aid of fiducials present in the pre-operative CBCT. This allows a fixture to be placed immediately prior to surgery, without the need for any fixture to be present in the pre-operative CBCT volume. As such, the present invention allows for use of any CBCT image to be used for performing guided surgery.

In a second embodiment of the invention, if a fixture is present in the CBCT scan, the present invention allows for correcting for imprecise placement of the fixture between pre-operative CBCT and a scan taken at the time of surgery-time.

In an embodiment of the invention, a method for referencing a tracking system's coordinate frame to a rigid body's coordinate frame is disclosed. The method involves providing the following (i) a 3D model depicting some of the surfaces of the rigid body, (ii) a probe with an affixed tracking reference component, and (iii) a rigidly affixed tracking reference component on the rigid body. The method tracks locations of the probe as it moves along surfaces of the rigid body, and determines a transform that relates the probe locations to the 3D model of the rigid body.

In one embodiment a method is disclosed for referencing a tracking system's coordinate frame to a rigid body's coordinate frame. The method includes providing (i) a 3D data set depicting some of the surfaces of the rigid body, (ii) a probe with an affixed tracking reference component, (iii) a rigidly affixed tracking reference component on the rigid body, and (iv) an initial transform that approximately relates the probe locations to the 3D data set of the rigid body. The method tracks the locations of the probe as it moves along surfaces of the rigid body and visually depicts the probe location in relation to the 3D dataset. The system then determines a plurality of estimates of the error between a given probe location and a portion of the surfaces in the 3D dataset. Using that data, the system determines a transform that relates the probe locations to the 3D model of the rigid body.

In another embodiment, a method is disclosed for referencing a tracking system's coordinate frame to a rigid body's coordinate frame. the method includes providing a computer display and displaying on the display a 3D data set depicting multiple surfaces of the rigid body, the rigid body including a person's oral cavity and at least some of the surfaces corresponding to the person's teeth or jawbone. The method includes providing a probe with an affixed tracking reference component, the probe having a probe tip, and a rigidly affixed tracking reference component on the rigid body. A signal is received when the probe tip is placed against a surface of the multiple surfaces and an approximate first location of the probe and probe tip is displayed on the 3D data set of the rigid body based on an initial transform. A line is generated on the display that is orthogonal to the first location of the probe tip. A signal is received to move the line relative to the 3D data set to a second location which corresponds to the depicted location in the 3D data set of an image corresponding to the surface of the multiple surfaces. An error value is determined that corresponds to the difference in location of the first and second locations and the error value is stored. A signal is received when the probe tip is placed against second surface of the multiple surfaces. Another line is generated on the display that is orthogonal to the depicted location of the probe tip relative to the second surface. A signal is received to move the line relative to the 3D data set to a second location which corresponds to the depicted location in the 3D data set of an image corresponding to the second surface. An error value is determined that corresponds to the difference in location of the first and second locations of the line with respect to the second surface and the error value is stored. A transform is determined based on the error values that relates the probe locations to the 3D model of the rigid body.

The 3D model in the embodiments disclosed herein can be a surface extracted from a computed tomography image of a patient's anatomy.

In any of the embodiments, the tracking system's coordinate frame may be attached to an electromagnetic field generator and the tracking reference components may be electromagnetic sensor coils.

In any of the embodiments, the tracking system's coordinate frame may be attached to a stereo optical tracking system.

In any of the embodiments, the tracking reference components may include contrast patterns.

In any of the embodiments, the tracking reference components may be arrays of reflective spheres.

In any of the embodiments, the tracking reference components may be arrays of light-emitting devices.

The probe in the embodiments disclosed herein may be an instrument with a spherical tip or a conical point.

The rigid body in the embodiments disclosed herein may be a dental mandible or maxilla of a patient.

In the methods disclosed herein the probe may be traced along and around the patient's teeth or along and around the patients jaw bone.

In the embodiments, the estimate of error is a correspondence between a probe tip location and a plane in the 3D data set.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

The above and other aspects, features, and advantages of the present invention may be more apparent from the following more particular description of embodiments thereof, presented in conjunction with the following drawings.

DETAILED DESCRIPTION OF THE PREFERRED EMBODIMENTS

A better understanding of various features and advantages of the present methods and devices may be obtained by reference to the following detailed description of illustrative embodiments of the invention and accompanying drawings. Although these drawings depict embodiments of the contemplated methods and devices, they should not be construed as foreclosing alternative or equivalent embodiments apparent to those of ordinary skill in the subject art.

Figure 1:
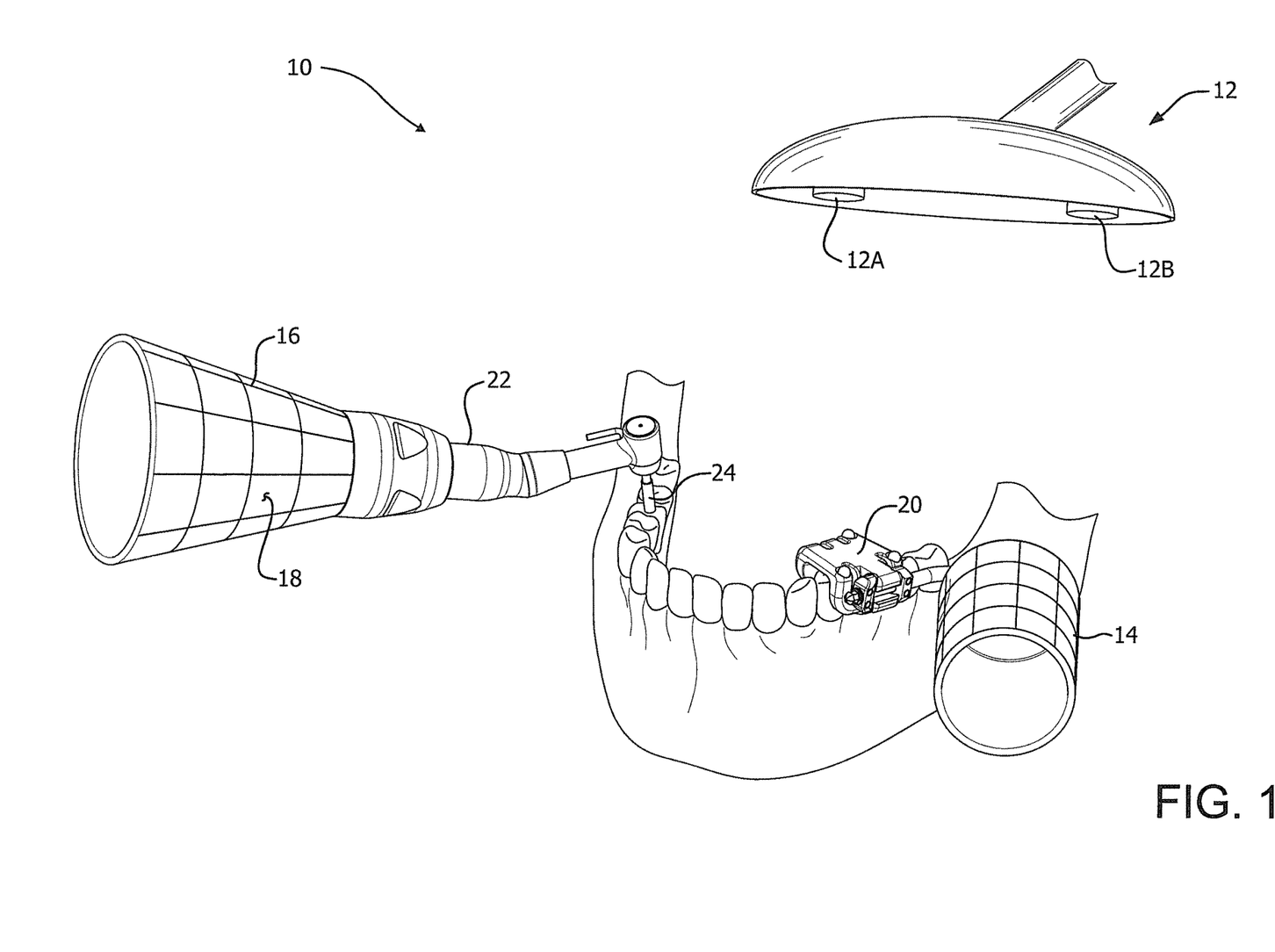
FIG. 1 illustrates probe tracing of the lower jaw of a patient according to the present invention.

Referring to the drawings, and initially to FIG. 1, a stereo tracking system 10 is disclosed which permits live tracking of a surgical tool relative to a pre-operative CBCT scan. The stereo tracking system 10 includes a stereo camera system 12, which may be any conventional system that is capable of capturing images that can be used for determining three dimensional location of an item being viewed. Typically such systems include at least two cameras 12A, 12B mounted above the surgical area. Those skilled in the art are familiar with such systems and, thus, no further discussion of such systems are necessary.

In a preferred embodiment, the stereo tracking system includes a lighting system, such as with blue or violet lighting, for providing illumination of a surgical or pre-surgical area. The lighting is configured to reflect off tracking reference components 14, 16 located in the surgical or presurgical area to facilitate capture by the cameras. The tracking reference components are objects that are covered with contrast patterns 18 that are unique to each type of tracking reference component (i.e., the patterns on a tracking reference component attached to a patient 14 are different than the patterns on the tracking reference component attached to an instrument). The illuminated contrast patterns 18 are observed by each of the two stereo tracking cameras, whose relative position is precisely known. Correspondences between each pair of images allow the tracking system to determine the location and orientation of each tracking reference component relative to the two tracking cameras. Suitable tracking reference components are described in detail in U.S. Pat. Nos. 9,402,691, 9,943,374, and 776,813D, the disclosures of which is incorporated herein by reference in their entirety.

In an embodiment, the stereo cameras 12 track three separate tracking reference components (not necessarily at the same time). One of the tracking reference components is the patient tracking component 14 which is attached rigidly and removably to the patient's teeth, such as with an oral fixture 20 that includes a thermoplastic impression of several teeth and described in U.S. Pat. No. 9,844,324, the disclosure of which is incorporated herein by reference in its entirety. The oral fixture 20 removably snaps or engages with the teeth and positions the patient tracking component 14 at a location that can been seen (captured) by the two cameras.

A second tracking reference component is the probe tracking component 16 which is rigidly attached to a probe device 22 which is used to trace portions of the patient's teeth as will be discussed below. The third tracking reference component is the surgical tool tracking component (not shown) that is rigidly attached to the surgical device (not shown) used to drill an osteotomy and deliver the implant into the patient jaw. The surgical device or tool could be the same instrument as the probe device 22 with the probe tip 24 switched to a drill bit. As such, the probe tracking reference component 16 for the probe device 22 and the surgical drill could be the same.

Prior to surgery, a cone beam computed tomography (CBCT) scan is acquired, including the patient's surgical anatomy of interest (usually the entire mandible or the entire maxilla). CBCT scans are well known in the art so no further discussion is needed. The surgeon imports the CBCT image into a software image guidance system, such as the X-Guide™ Surgical Guidance System sold by X-Nav Technologies, LLC. and defines the desired location and orientation of the implants (i.e., creates a surgical plan). The surgeon also defines the locations of the two most distal molars (or where they would be if missing) and the most mesial location on the dental arch.

Figure 2:
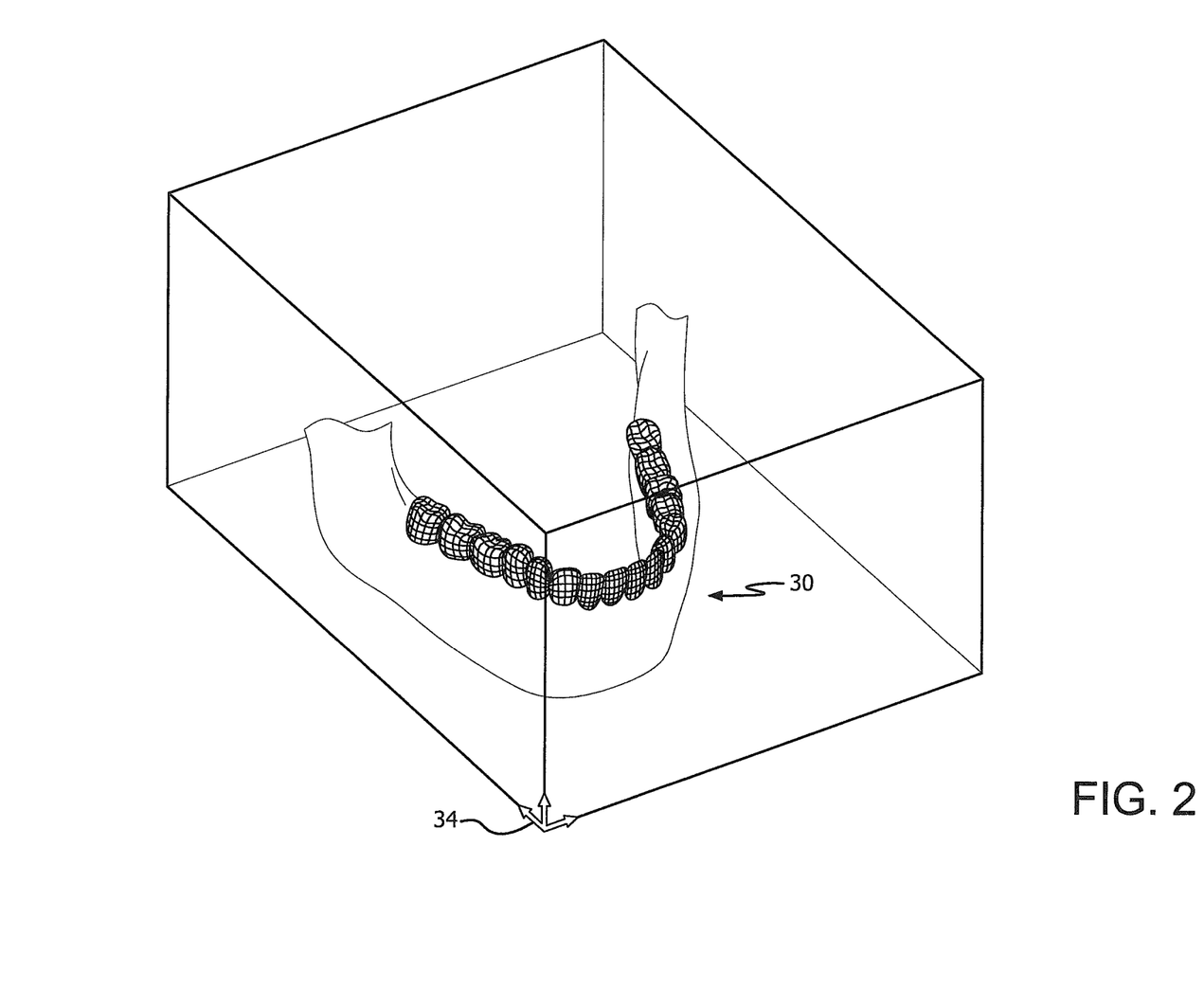
FIG. 2 is a pre-operative CBCT-derived iso-surface of a patient's jaw with the pertinent features, such as the teeth stored as a 3D mesh model.

Next, the CBCT is processed using a computer graphics algorithm, such as marching cubes which is a high resolution computer graphics 3D surface constructions algorithm published by William E. Lorensen and Harvey E. Cline in: Computer Graphics, Vol. 21, Nr. 4, July 1987, which is used to extract a polygonal mesh from the CBCT scan (which is incorporated herein by reference in its entirety). Using the marching cubes algorithm, an iso-surface 30 at the level of the bone-air transition can be automatically extracted. See FIG. 2. An 800 HU (Hounsfield Unit), which is a scale based on radiodensities of various materials, is typically a suitable value for the iso-surface. The HU scale is well known to those skilled in the art. This iso-surface 30 that is created is a 3D surface model of the patient's jaw and teeth.

On the day of surgery, the surgical staff performs a series of calibrations. The staff first calibrates the probe device 22. As mentioned above the probe device 22 has an attached probe tracking reference component 16, preferably attached to the handle. The probe device 22 includes a probe tip 24 that has a small, precise, stainless steel sphere. The calibration is performed using the probe device 22 and a calibration plate. The calibration plate is a tracking reference component with a flat surface and a conical divot formed in it for receiving the sphere. The flat surface includes contrast patterns 18 similar to the ones described above, for example, the contrast patterns described in U.S. patent application Ser. No. 29/519,642 and U.S. Pat. No. 9,943,374 (the disclosures of which are incorporated herein by reference in their entirety). With the camera tracking system on, the probe device's sphere tip is inserted into the conical divot and the probe device is pivoted with respect to the calibration plate, generating relative estimates between the probe tracking reference component 16 and the calibration plate (for example, about 500 estimates). The location of the pivot point (i.e., the center of the spherical tip) is solved with respect to the probe tracking reference component's coordinate system by solving a linear least-squares system of equations such that the residual error over all relative estimates is minimized. Once the location of the probe tip sphere is known, the tracking system can determine the location of the center of the probe tip sphere based on the detected location of the probe tracking reference component 16.

The surgical staff also calibrates the drill that will be used to drill the osteotomy and to place the implant. The drill to be used has a tracking reference component integrated into the handle. As mentioned above, the drill and the probe device may be the same tool with only the tips switched. The drill calibration is performed in two steps. In the first step, a special drill bit, with an attached tracking reference component, is inserted into the chuck of the drill. The bit is rotated slowly (e.g., about 10 RPM) in such a way that the tracking system (i.e., the cameras 12A, 12B) can capture both the patient tracking reference component 14 and the probe tracking reference component 16 and determine a suitable number of relative estimates between those two tracking reference components 14, 16 (e.g., approximately 500 estimated calculations.) The image guidance system uses a linear least squares system of equations to solve for the axis of rotation that minimizes the residual error over all accumulated estimates.

In the second step, a drill bit (or the implant) is inserted into the chuck of the drill and its tip is held against and perpendicular to the flat surface of the calibration plate. The tracking system is then activated and the doctor or technician moves (rotates and pivots) the tool about its tip so that the cameras can capture the relative positon between the calibration plate and the drill tracking reference component. The combination of these steps determines the axis and location of the tip of the drill bit with respect to the drill tracking reference component. The calibration procedure is described, for example, in U.S. patent application Ser. No. 14/209,500, the disclosure of which is incorporated herein by reference in its entirety. The second step is repeated for each drill bit or implant used during the surgery.

When the patient arrives, the surgical staff attaches the patient tracking reference component 14 to the patient by affixing it to the patient's teeth using the oral fixture described above.

Using the probe device 22, the surgeon holds the probe tip near each of the three arch locations that were defined during planning, and interacts with the software to indicate that the tip is in the desired location. By simultaneously tracking both the patient tracking reference component 14, and the probe tracking reference component 16, the tracking system can locate where the probe tip 24 is with respect to the patient tracking reference component 14, which defines a floating coordinate system (coordinate system 32 in FIG. 3) because it has not yet been related to the patient's CBCT scan. Probing each of the three arch locations defines three notional, but inaccurate correspondences between the CBCT-derived coordinate system and the floating patient coordinate system, which is a sufficient number to perform absolute orientation to derive a best-fit transform. While too inaccurate in most cases to support surgical navigation, this provides an initial estimate of the true transform that relates the floating patient coordinate system to the pre-operative CBCT coordinate system (coordinate system 34 in FIG. 2). This initial estimate of the transform serves a dual purpose: (i) it allows for meaningful visual feedback while the surgeon is performing the probe trace in the next step, and (ii) once the probe trace has been performed, it facilitates the refinement of the transform because the initialization can be assumed to be close to the final transform.

Figure 3:
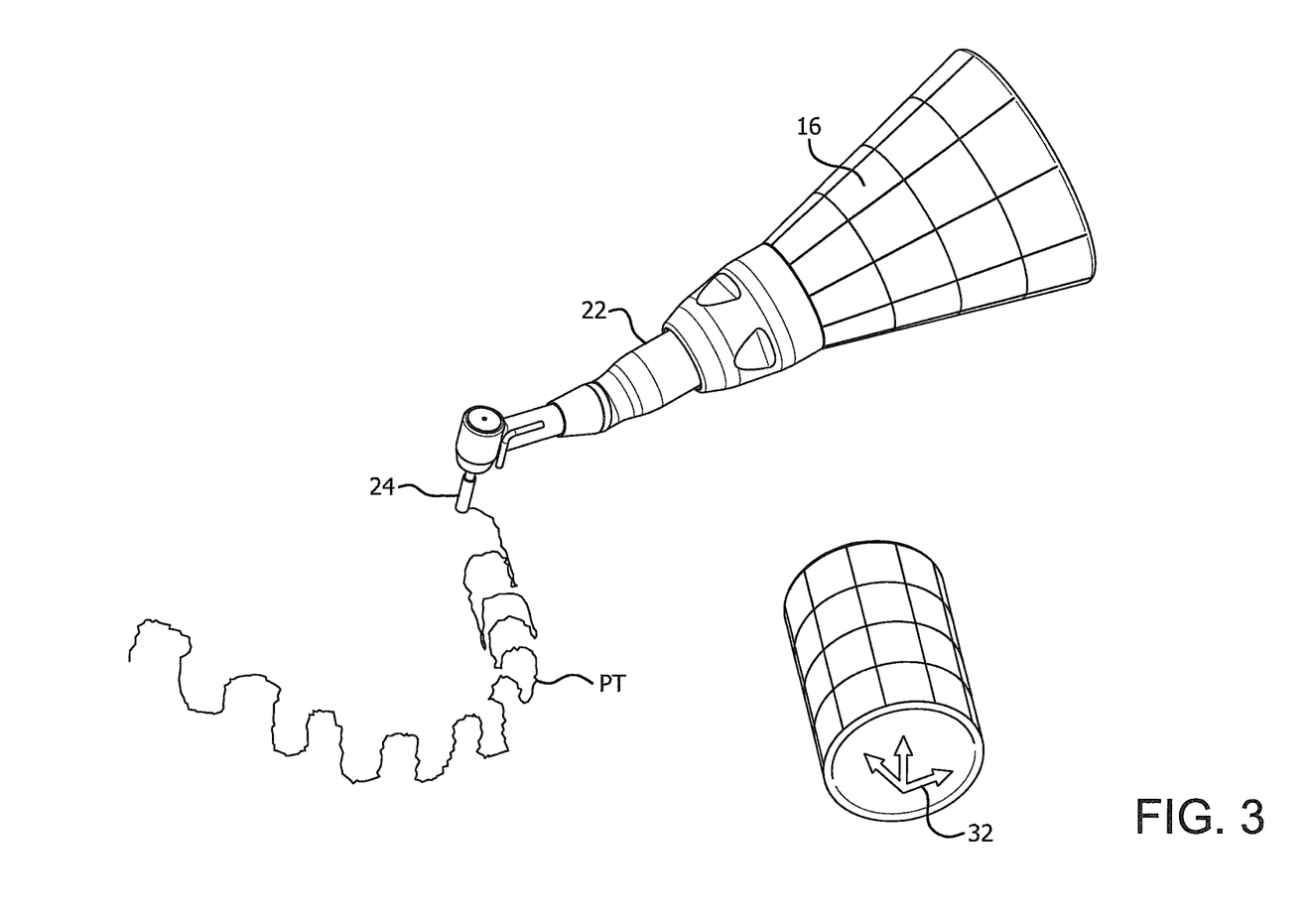
FIG. 3 illustrates the trace of the teeth of the lower jaw in FIG. 1 created by the probe during surgery.

The surgeon now begins the probe trace. Referring to FIG. 3, the surgeon places the probe tip on a tooth surface, and interacts with the tracking system to indicate the beginning of a probe trace. The surgeon slowly traces the probe's spherical tip over each of the patient's exposed teeth, tracing points on the occlusal, buccal, and lingual surfaces. With the tip of the probe still in contact with a tooth surface, the surgeon interacts with the tracking system to indicate the end of the trace. A sample of the probe trace is shown in FIG. 3 and identified as PT. Throughout the probe trace process, the tracking system simultaneously estimates the locations of the probe tracking reference component 16 on the probe device 22 and the patient tracking reference component 14 on the patient, which in combination with the probe calibration generates a sequence of estimates of 3D points near (one probe sphere radius away from) the surface of the teeth. These probe trace points PT are still in a floating patient coordinate system (FIG. 3), and not yet related to the CBCT coordinate system.

Figure 4:
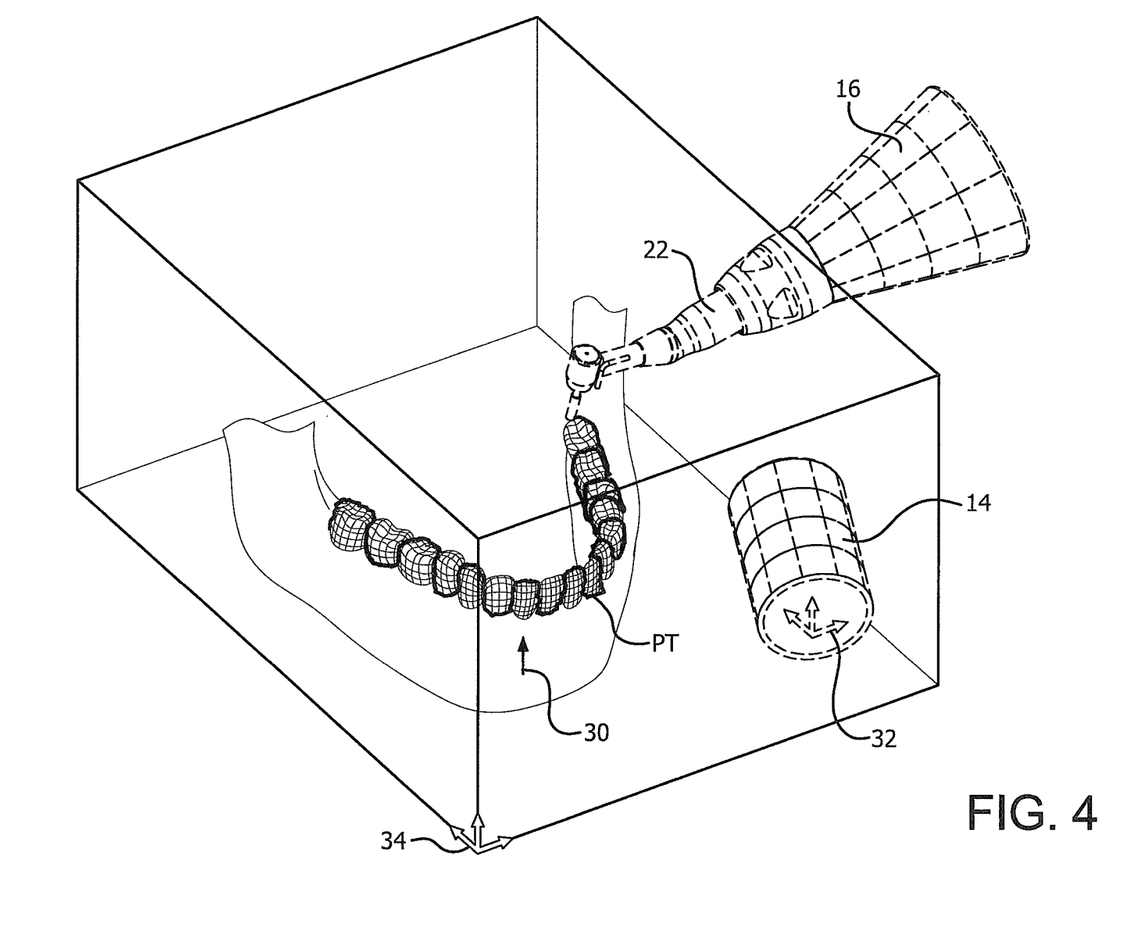
FIG. 4 illustrates the alignment/registration of the probe trace of FIG. 3 with the pre-operative CBCT scan.
Figure 5A:
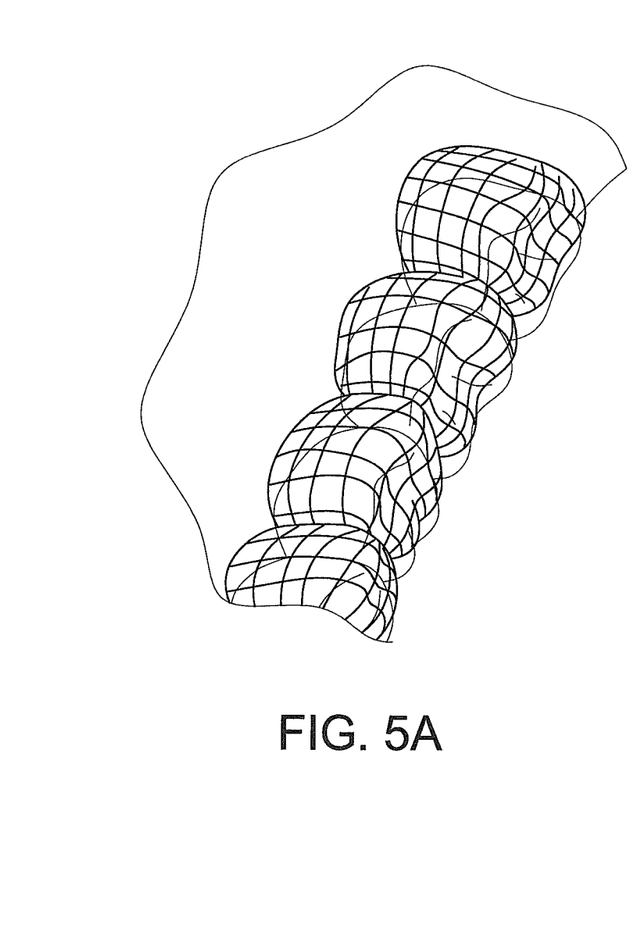
FIG. 5A illustrates an enlargement of a portion of the probe trace prior to alignment with a portion of the teeth in the CBCT scan.
Figure 5B:
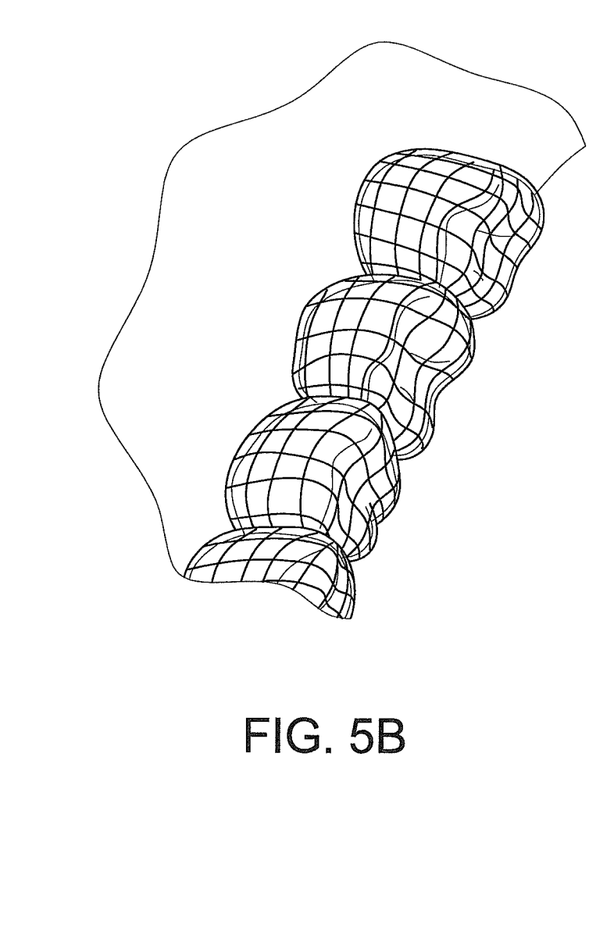
FIG. 5B illustrates the portion of the probe trace of FIG. 5A after alignment with the teeth in the CBCT scan.

The sequence of probe trace point estimates are processed in combination with the jaw and teeth iso-surfaces automatically extracted from the CBCT volume. The first step in this process is to offset (dilate) the iso-surface by the radius of the probe tip. FIG. 5A. In the preferred embodiment, this is done by offsetting each vertex outward along its normal direction, but in alternate embodiments this could be done by 1) creating a supersampled binary volume mask enclosed by the isosurface, 2) dilating the volume mask by adding any voxel whose voxel center is within one radius of an original volume mask voxel, 3) creating a new isosurface from the dilated voxel mask. In doing this offsetting, an ideal alignment of the probe trace points to the offset iso-surface would place all probe trace points in contact with (or very near to) the dilated iso-surface. The second step in this process is to align the probe trace points to the dilated iso-surface. FIG. 5B. The system uses a well-known iterative closest point (ICP) algorithm, which is typically used for aligning two surfaces to each other. ICP algorithm determines the transform that best aligns the trace points to the dilated iso-surface, and in doing so, determines the relationship between the floating coordinate system 32 and the CBCT coordinate system 34. FIG. 4. At this stage, whenever the probe tracking reference component 16 is tracked by the system simultaneously with the patient tracking reference component 14, the location of the probe sphere center can be related back to a 3D coordinate 34 in the CBCT volume, and the sphere center depicted with respect to the CBCT depiction of the patient anatomy (FIG. 4). Similarly, whenever the drill tracking reference component is tracked simultaneously with the patient tracking reference component 14, the axis and tip of the drill bit (or implant) can be related back to the CBCT volume, and the drill's location and orientation can be depicted with respect to the CBCT depiction of the patient anatomy and implant plan.

The surgeon is now free to use the drill to deliver the implant using any conventional dental implant guidance system, such as the X-Guide® Guidance System described in the above referenced patents.

There are several variations that are possible in the present invention. For example, the probe tip does not need to be spherical, it can, instead, have a defined point. As mentioned above, the probe device and the drill can be the same device, provided a sphere-ended or pointed drill bit is used. Other bit geometries can be used with diminished accuracy.

Figure 8:
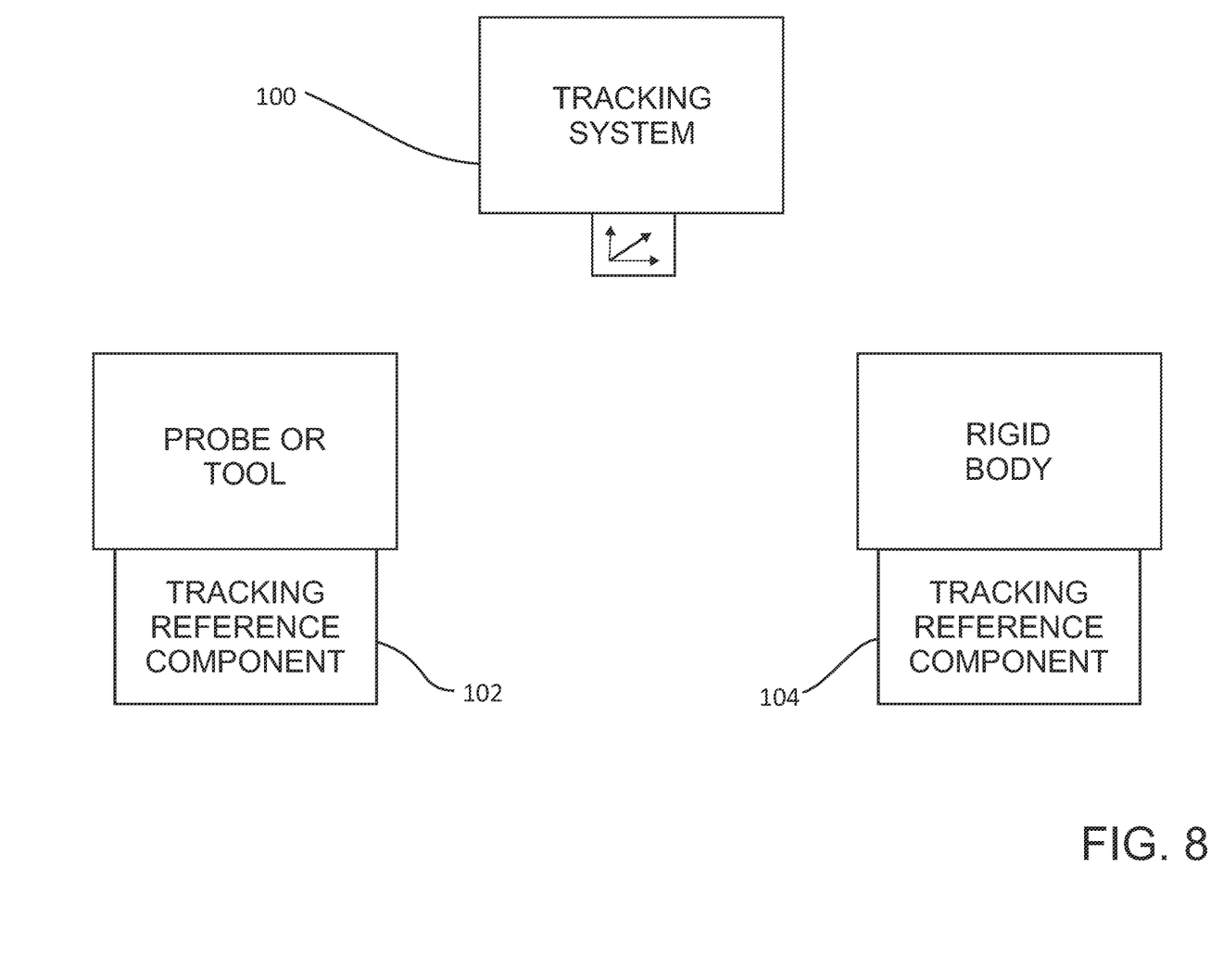
FIG. 8 is a schematic representation of tracking system for determining the location and orientation of two tracking reference components in a single reference frame.

The present invention does not need to be used with an optical stereo tracking system. Instead, with reference to FIG. 8, any tracking system 100 that can determine the location and orientation of two tracking reference components 102, 104 in a single reference frame is suitable for use with the above described fiducial free tracking system. Electromagnetic trackers (electromagnetic field generators) can be used as the tracking system 100 if an E/M sensor coil is attached to the probe device as the probe tracking reference component 102 and to the patient as the patent tracking reference component 104. Alternately the field generator may be attached to either the probe device or the patient, with a sensor being attached to the other. Likewise mechanical encoding arms can be used to track the probe and/or the patient.

The probe tracking reference component 16 attached to the probe device does not always need to determine the probe device's location in a six degrees of freedom sense. A five degrees of freedom tracking reference component can be used if it is aligned such that the axis of the center passes through the probe sphere center or tip. A three degrees of freedom tracking reference component can be used if it is co-located with the probe sphere center or tip.

There are many variants on providing initialization transforms. No initialization transform is strictly needed. Initialization can be provided by using user-defined point correspondences between points on the trace and corresponding points on the CT, or by interactive manipulation of the trace in the CT coordinate frame.

Initialization by manipulation of the trace can be performed by graphically depicting the trace overlaid upon a 2D or 3D representation of the CBCT scan (e.g., 2D slices possibly including iso-surface outlines, volume renderings or iso-surface renderings), the trace being related to the CBCT scan by its current rigid transform estimate. The user can interact with a system to adjust the rigid transform, effectively translating or rotating the trace as a whole with respect to the underlying CT representation until they are visually aligned. This process can be assisted by correspondences consisting of points selected on the trace and corresponding points selected on the CT representation.

Existing tracking systems can also provide initialization through use of fiducials identified in the Pre-operative CBCT scan. In these cases, the probe trace can be used to refine the transform and correct for any errors due to removal and replacement of the patient attachment between CBCT and surgery.

Figure 6A:
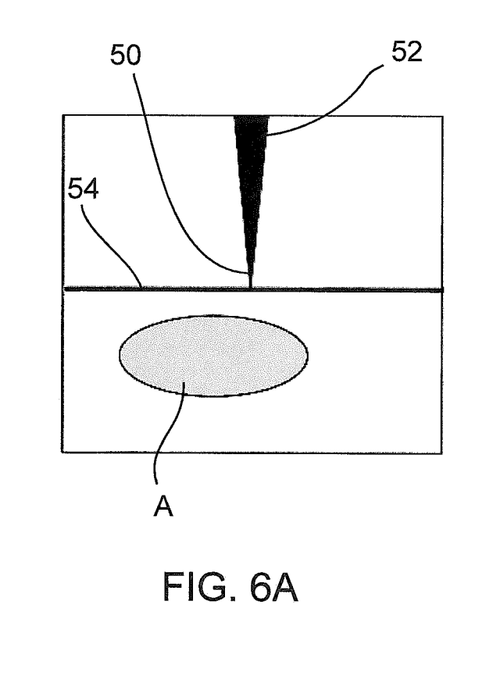
FIG. 6A illustrates visualization of the interactive transform refinement prior to the alignment step.
Figure 6B:
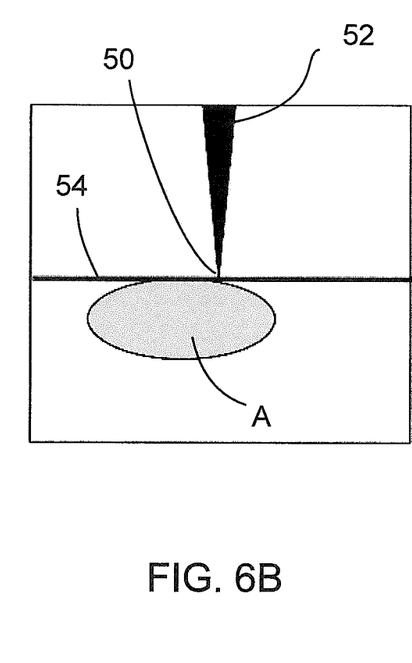
FIG. 6B illustrates visualization of the interactive transform refinement after the alignment step.
Figure 6C:
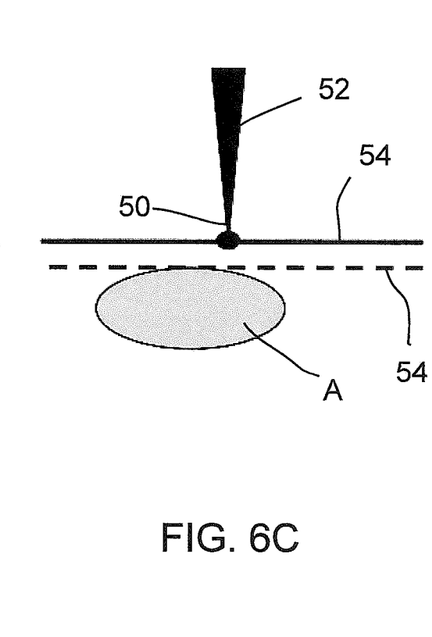
FIG. 6C illustrates extraction of the point and plane for the interactive transform refinement
Figure 7A:
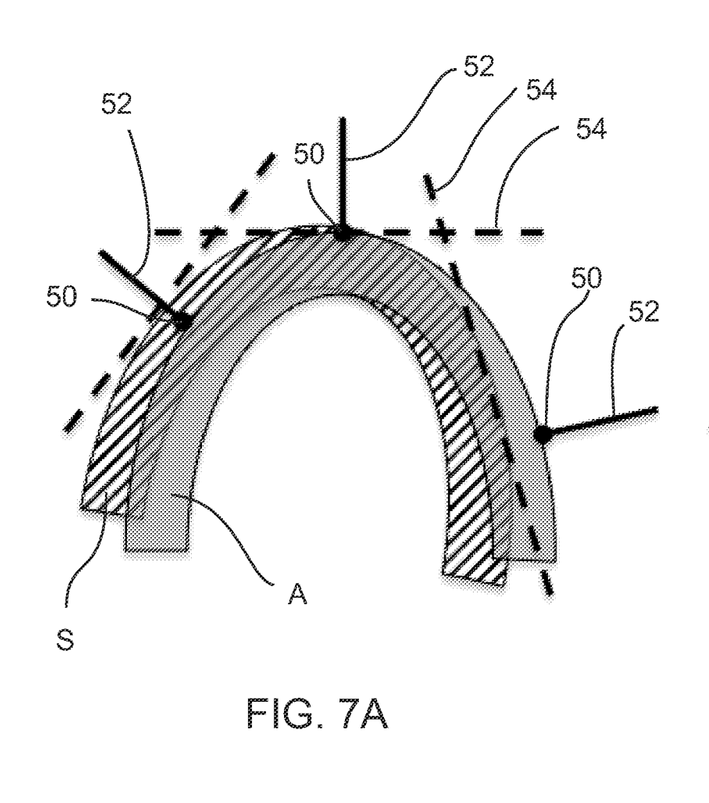
FIG. 7A illustrates several probe location points and corresponding CT planes prior to alignment by the interactive transform refinement.
Figure 7B:
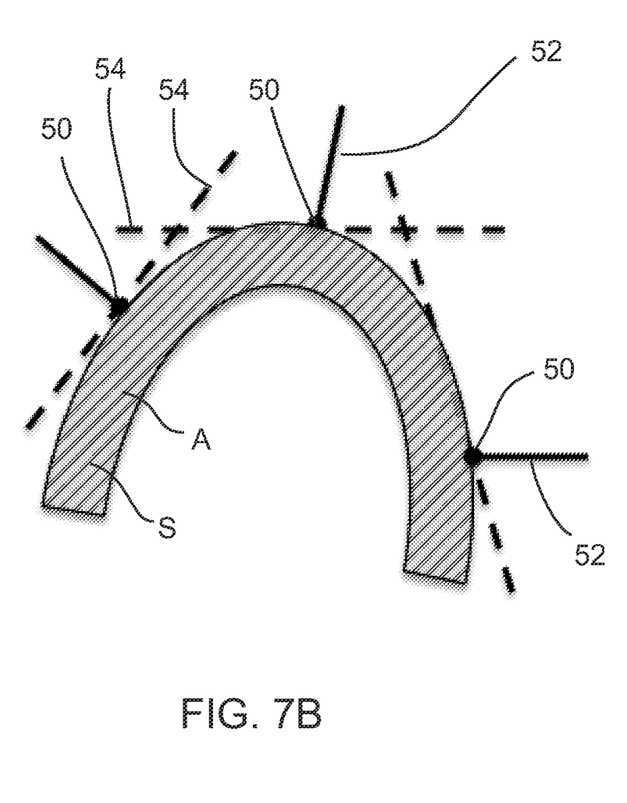
FIG. 7B illustrates several probe location points and corresponding CT planes subsequent to alignment by the interactive transform refinement

Additional interactive refinement to initialization can be performed prior to or as an alternative to performing automated trace alignment. This process is depicted in FIG. 7A and FIG. 7B. In one such method, the surgeon places the tip 50 of a pointed probe 52 in contact with a point on the anatomy A in such a way that the probe tip 50 is aligned with its axis approximately normal to the surface it is in contact with. The surgeon indicates to the system to select this tip location as a point for refinement. A set of interactive CT representations is displayed. In one embodiment, this is a set of 3 orthogonal slices S as depicted in FIG. 6A, oriented with respect to the estimated probe tip's canonical axes (whose origin is at the probe tip, whose Z axis is aligned with the probe tip axis, with the probe handle aligned in the X/Z plane). The system places a line 54 on the display, drawn orthogonal to Z on each slice, which depicts the projection of a plane orthogonal to the probe tip axis. The surgeon can move this line up or down the probe axis until it just touches the surface of the anatomy A whose transition is visible in the CT, in an attempt to correct for any error in this axis. For example, the surgeon can use the roller wheel on a mouse to move the line upwards or downwards on the display to align it with the surface of the anatomy A. Once this adjustment is complete, at which point the system would look similar to FIG. 6B, the surgeon interacts with the system to finish the adjustment, and the system stores 1) the plane equation in CT coordinates, and 2) the probe tip location and direction in patient tracker coordinates as depicted in FIG. 6C. The surgeon defines additional points and corresponding planes in the same way, after which time, the system performs an optimization over the rigid body transform T relating the patient tracker coordinate system to the CT coordinate system. In one embodiment, this optimization minimizes the sum of squared distances between the planes and their corresponding patient tracker points transformed into CT coordinates via transform T. Variants to this optimization can add constraints on T and/or impose penalties on the distance between the transformed point and the center of the plane (where the original Z axis intersected the plane) in order to reduce the number of correspondences required or to improve robustness or convergence speed. The surgeon can repeat this process one or more times in order to further refine the estimate of T. This process can either be used to improve the initialization to, and therefore the robustness of automated trace alignment, or can be used instead of automated trace alignment. This can be desirable, e.g., in fully edentulous patients, where soft tissue surfaces probed with a spherical probe are difficult to automatically locate on the CT, and where instead a pointed probe can puncture through to the hard tissue, which can be more easily discerned interactively by the surgeon.

The method is not restricted to oral anatomy. It can be used on any rigid body part. Rigid does not necessarily mean hard. The probe trace could be performed on soft tissue as well, provided the deformation is limited between when the 3D model is created and when the trace is performed.

The method is not restricted to 3D models derived from a CBCT or CT scan of a patient. For example, the above described method would work equally well for relating the tracking system to a pre-operative intra-oral optical scan with respect to which an implant plan can be defined pre-operatively.

The method is not restricted to medical applications. It could, for example, be used in registering a known mechanical part on a CNC milling machine, prior to secondary machining.

While the above description refers to a surgical tool or instrument that includes a drill, the term "surgical instrument" or "surgical tool" is intended to cover other tools used during intraoral procedures, such as ablation tools for ablating tissue, including third molars in children.

The system or systems described herein may be implemented on any form of computer or computers and the algorithms and programs may be implemented as dedicated applications or in client-server architectures, including a web-based architecture, and can include functional programs, codes, and code segments. The computer system of the present invention may include a software program be stored on a computer and/or storage device (e.g., mediums), and/or may be executed through a network. The computer steps may be implemented through program code or program modules stored on a storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The computer processes herein may be described in terms of various processing steps. Such processing steps may be realized by any number of hardware and/or software components that perform the specified functions. For example, the described embodiments may employ various integrated circuit components, e.g., memory elements, processing elements, logic elements, look-up tables, and the like, which may carry out a variety of functions under the control of one or more microprocessors or other control devices. Similarly, where the elements of the described embodiments are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the embodiments of the invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the steps of all methods described herein are performable in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

What is claimed is:

1. A method for referencing a tracking system's coordinate frame to a coordinate frame of a 3D model of a rigid body, the rigid body comprising at least a portion of a patient's oral cavity, the method locating a patient tracking device with respect to a cone-beam computer tomography (CBCT) volume without the use of any fiducial located on the patient, the method comprising the steps of:
    providing a 3D model depicting at least a portion of surfaces within a patient's oral cavity, the surfaces including at least three defined anatomical features;
    providing a tracking system;
    providing a probe with an affixed probe tracking reference component, the probe having a probe tip;
    detecting with the tracking system the location of a fiducial free patient tracking reference component rigidly and removably affixed to a location relative to a patient's oral cavity, the location being determined without the use of any fiducial material on the patient tracking device;

receiving a signal in the tracking system when the probe tip is at a location within the patient's oral cavity corresponding to one of the at least three defined anatomical features, detecting the location of the probe tracking reference component with the tracking system in response to the signal;

determining a three-dimensional location of the probe tip associated with each detected location of the probe tracking reference component, storing the three dimensional locations of the probe tip corresponding to the at least three anatomical locations;

determining an initial transform that relates the three-dimensional location of the probe tip associated with each detected location to the at least three defined anatomical features in the 3D model;

receiving a signal in the tracking system indicative of the commencement of a probe trace;

tracking with the tracking system the locations of the of the probe tracking reference component as the probe tip traces a path along surfaces of the patient's oral cavity and determining three dimensional locations of the probe tip at a plurality of sequential points along the probe trace path using the initial transform;

receiving a signal in the tracking system indicative of the ending of the probe trace; and determining a final transform that aligns the three dimensional locations of the probe tip at the plurality of sequential points with corresponding points in the 3D model.

2. The method of claim 1, wherein the 3D model is a surface extracted from a computed tomography image of a portion of a patient's oral cavity.

3. The method of claim 1, wherein the tracking system is an electromagnetic field generator and the affixed probe tracking reference component and the patient tracking reference component are electromagnetic sensor coils.

4. The method of claim 1, wherein the tracking system is a stereo optical tracking system.

5. The method of claim 4, wherein the affixed probe tracking reference component and the patient tracking reference component include contrast patterns.

6. The method of claim 4, wherein the affixed probe tracking reference component and the patient tracking reference component include reflective spheres.

7. The method of claim 4, wherein the affixed probe tracking reference component and the patient tracking reference component include light-emitting devices.

8. The method of claim 1, wherein the probe is an instrument with a spherical tip.

9. The method of claim 1, wherein the probe is an instrument with a tip that includes a conical point.

10. The method of claim 1, wherein the 3D model includes a scan of a dental mandible or maxilla of a patient's oral cavity.

11. The method of claim 10, wherein the probe is traced along and around the patient's teeth.

12. The method of claim 10, wherein the probe is traced along and around the patient's jaw bone.

13. A method for referencing a tracking system's coordinate frame to a coordinate frame of a 3D data set of a rigid body, the rigid body comprising at least a portion of a patient's oral cavity, the method locating a patient tracking device with respect to a cone-beam computer tomography (CBCT) volume without use of any fiducial located on the patient, the method comprising the steps of:

providing a 3D data set depicting surfaces of a portion of a patient's oral cavity, the surfaces including at least three defined anatomical features;

providing a tracking system;

providing a probe with an affixed probe tracking reference component, the probe having a probe tip;

detecting with the tracking system the location of a fiducial free patient tracking reference component rigidly and removably affixed to a location relative to a patient's oral cavity, the location being determined without the use of any fiducial material on the patient tracking device;

providing an initial transform that approximately relates the probe tip locations to the 3D data set of the portion of the patient's oral cavity;

receiving a signal in the tracking system when the probe tip is at a location within the patient's oral cavity corresponding to one of the at least three defined anatomical features, detecting the location of the probe tracking reference component with the tracking system in response to the signal;

determining a three-dimensional location of the probe tip associated with each detected location of the probe tracking reference component, storing the three dimensional locations of the probe tip corresponding to the at least three anatomical locations;

visually depicting on a display the three dimensional location of the probe tip in relation to the 3D data set for the at least three anatomical locations;

calculating a plurality of estimates of the error between the three dimensional probe tip location of at least one anatomical location and a corresponding anatomical feature in the 3D data set; and determining an initial transform that relates the three dimensional location of the probe tip associated with each detected location to the at least three defined anatomical features in the 3D data set;

receiving a signal in the tracking system indicative of the commencement of a probe trace;

tracking with the tracking system the locations of the of the probe tracking reference component as the probe tip traces a path along surfaces of the patient's oral cavity and determining three dimensional locations of the probe tip at a plurality of sequential points along the probe trace path using the initial transform;

receiving a signal in the tracking system indicative of the ending of the probe trace; and determining a final transform that aligns the three dimensional locations of the probe tip at the plurality of sequential points with corresponding points in the 3D model.

14. The method of claim 13, wherein the estimate of error is a correspondence between at least one three dimensional probe tip location and a plane in the 3D data set.

15. The method of claim 13, wherein the 3D data set is generated from a CT scan of at least a portion of a patient's oral cavity, and wherein the surfaces are teeth or portions of a patient's jawbone, and wherein the approximate location of the probe tip relative to the 3D data is depicted on the display; wherein prior to the step of calculating a plurality of estimates, the method further comprising the steps of generating a line on the display that is orthogonal to the three dimensional probe tip location for at least one anatomical location, the line being at a first location; moving the line on the display relative to the 3D data set to a second location corresponding to the location on the display of a one of the anatomical features in the data set; calculating a distance of movement from the first location to the second location, and wherein at least one of the estimates of error is determined based on the calculated distance.

16. A method for referencing a tracking system's coordinate frame to a coordinate frame of a 3D data set of a rigid body, the rigid body comprising at least a portion of a patient's oral cavity, the method locating a patient tracking device with respect to a cone-beam computer tomography (CBCT) volume without the use of any fiducial located on the patient, the method comprising the steps of:
 a. providing a tracking system including a computer display;
 b. displaying on the display a 3D data set depicting multiple surfaces of portions of a patient's oral cavity and at least some of the surfaces corresponding to the patient's teeth or jawbone, the surfaces including at least three defined anatomical features;
 c. providing a probe with an affixed probe tracking reference component, the probe having a probe tip;
 d. detecting with the tracking system the location of a fiducial free patient tracking reference component rigidly and removably affixed to a location relative to a patient's oral cavity, the location being determined without the use of any fiducial material on the patient tracking device;
 e. receiving in the tracking system a first signal when the probe tip is at a location within the patient's oral cavity corresponding to one of the at least three defined anatomical features, and determining a three dimension location of the probe tip based on the three dimensional location of the probe tracking reference component;
 f. depicting on the display an approximate first location of the probe and probe tip on the 3D data set based on an initial transform that relates the three-dimensional location of the probe tip associated with the defined anatomical feature to at least one of the at least three defined anatomical features in the 3D model;
 g. generating a line on the display that is orthogonal to the first location of the probe tip;
 h. moving the line on the display relative to the 3D data set to a second location which corresponds to a depicted location in the 3D data set of an image corresponding to the surface in the patient's oral cavity;
 i. determining an error value corresponding to the difference in location of the first and second locations and storing the error value;
 j. receiving in the tracking system a second signal representing location coordinates of the probe tracking reference component when the probe tip is placed against another surface in the patient's oral cavity and repeating steps f through i for the second signal; and
 k. determining a final transform from the error values that relates the probe locations to the 3D data set.

* * * * *